United States Patent [19]

Adams

[11] Patent Number: 5,285,676
[45] Date of Patent: Feb. 15, 1994

[54] AIR-FUEL RATIO MEASUREMENT APPARATUS AND METHOD THEREFOR

[75] Inventor: Neil J. Adams, West Bloomfield, Mich.

[73] Assignee: Motorola, Inc., Schaumburg, Ill.

[21] Appl. No.: 923,425

[22] Filed: Aug. 3, 1992

[51] Int. Cl.$^5$ ............................................. G01N 31/12
[52] U.S. Cl. ..................................... 73/23.32; 73/116; 250/339
[58] Field of Search ................... 73/116, 23.32, 23.33; 123/672; 250/339

[56] References Cited

U.S. PATENT DOCUMENTS

| | | | |
|---|---|---|---|
| 4,179,606 | 12/1979 | Nakauchi et al. | 250/339 |
| 4,435,149 | 3/1984 | Astheimer | 431/12 |
| 4,444,169 | 4/1984 | Kirisawa et al. | 123/344 |
| 4,468,949 | 9/1984 | Linder et al. | 73/35 |
| 4,560,873 | 12/1985 | McGowan et al. | 250/339 |
| 4,779,455 | 10/1988 | Kuroiwa et al. | 73/116 |
| 4,887,574 | 12/1989 | Kuroiwa et al. | 123/425 |
| 4,919,099 | 4/1990 | Extance et al. | 123/425 |
| 5,050,556 | 9/1991 | Williams et al. | 123/425 |

FOREIGN PATENT DOCUMENTS

| | | | |
|---|---|---|---|
| 304230 | 2/1989 | European Pat. Off. | 250/339 |
| 0304230 | 2/1989 | United Kingdom . | |

Primary Examiner—Jerry W. Myracle
Attorney, Agent, or Firm—Phillip H. Melamed; John H. Moore

[57] ABSTRACT

An apparatus, and corresponding method, for directly measuring air-fuel ratio of a combustion process, in an internal combustion engine is described. The apparatus includes a first electromagnetic wave sensor (105) that provides a first signal (107), representative of light intensity emitted at a first wavelength, and a second electromagnetic wave sensor (115) that provides a second signal (117), representative of light intensity emitted at a second wavelength. A ratio circuit (111, 121, 125) combines an integral of the first signal (107), and an integral of the second signal (117), and provides an air-fuel ratio signal, (127) indicative of the air-fuel ratio during the combustion process.

19 Claims, 2 Drawing Sheets

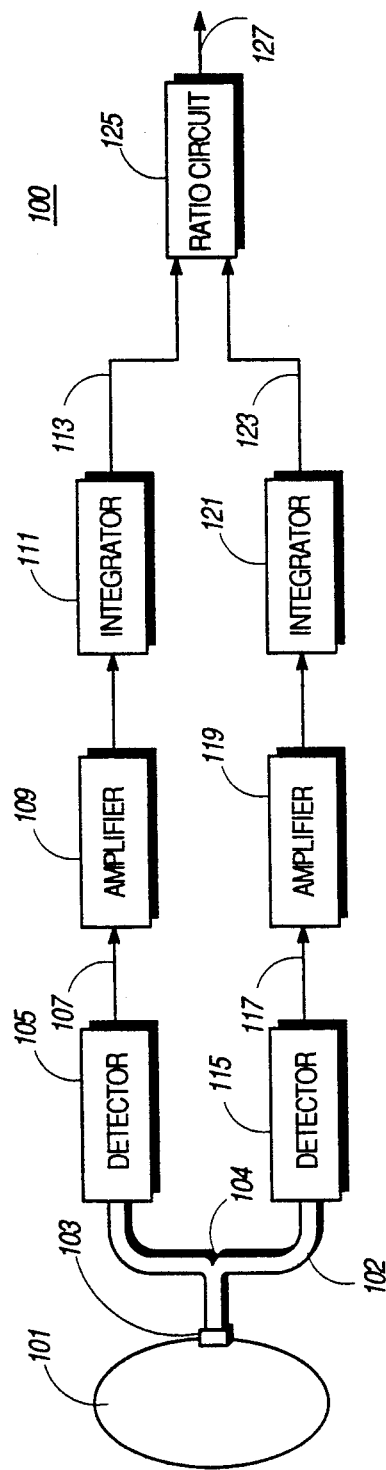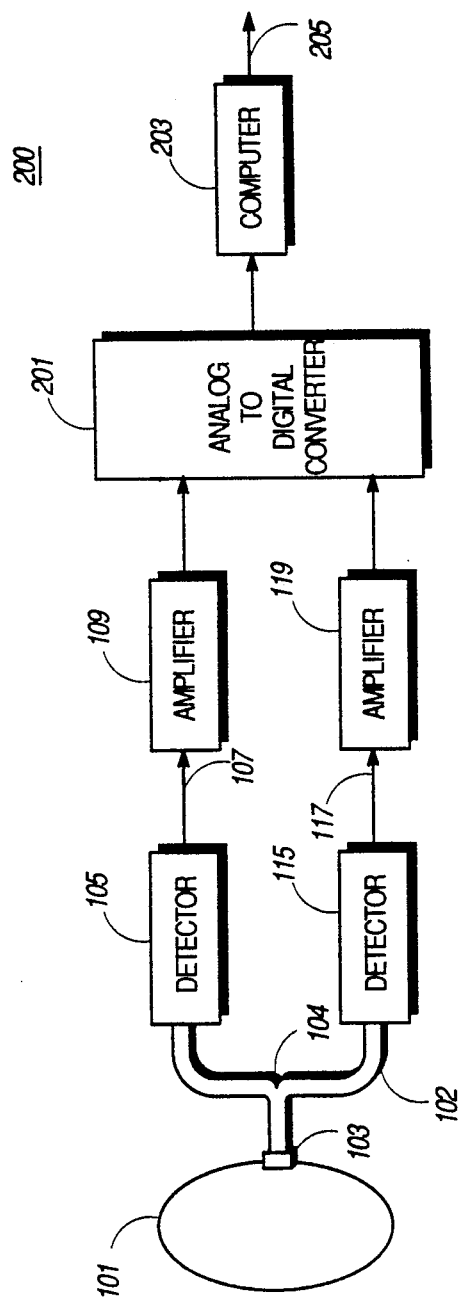

AIR-FUEL RATIO MEASUREMENT APPARATUS AND METHOD THEREFOR

FIELD OF THE INVENTION

This invention is generally directed to the field of recognition of air-fuel ratio in an internal combustion process, and more particularly to the direct measurement of air-fuel ratio of a combustion gas mixture, in an internal combustion engine on the basis of electromagnetic wave observation.

BACKGROUND OF THE INVENTION

In an internal combustion engine, it is generally useful to measure an air-fuel ratio of a combustion process to efficiently control the engine's performance. In particular, by controlling the air-fuel ratio such that the mixture for combustion is stoichiometric, exhaust emissions are reduced by enabling a downstream catalytic converter to operate with maximum conversion efficiency for the principal exhaust constituents.

Various schemes have been used to measure the electromagnetic energy, in the form of light, emitted during the combustion process for indirectly determining or controlling air-fuel ratio. These previous schemes have not been sufficiently simple in their implementation. For instance, one approach suggests determining air-fuel ratio by considering the phase difference between peak values of the outputs of two photoelectric sensors tuned to receive substantially different wavelengths. Thus both the peak values of light intensity and the phasing at which they occur must be detected. This adds additional complexity and inaccuracy. The final result is a non-linear relationship between the measured parameter and the air-fuel ratio. To convert this non-linear result into usable form, requires additional resources. This also adds inaccuracy to the determination process. Another approach uses the outputs of two photoelectric sensors whose peak responses are at different frequencies. The ratio of the logarithm of the output of these sensors is considered at a specific point in the combustion process. The magnitude of the minimum of the signal after the peak value of the signal is claimed to be related to the NOx content of exhaust gas. In this approach, the air-fuel ratio is not directly derived, but inferred from the resulting signal. This approach is both complex and indirect.

Other schemes that directly measure intensity of emitted electromagnetic radiation are inaccurate because of the contamination of the measuring device, mainly due to soot deposits that vary according to engine operating conditions.

What is needed is a more robust and accurate apparatus, or method that is simpler to implement, for directly measuring the air-fuel ratio of a combustion process in an internal combustion engine.

SUMMARY OF THE INVENTION

An apparatus, and corresponding method, for directly measuring air-fuel ratio of a combustion process, in an internal combustion engine is described. The apparatus includes a first electromagnetic wave sensor providing a first signal, representative of light intensity emitted at a first wavelength, and a second electromagnetic wave sensor, providing a second signal representative of light intensity emitted at a second wavelength. A ratio circuit combines an integral of the first signal, and an integral of the second signal, and provides an air-fuel ratio signal, indicative of the air-fuel ratio during the combustion process.

BRIEF DESCRIPTION OF THE DRAWINGS

FIG. 1 is a schematic block diagram of an apparatus for directly measuring air-fuel ratio of a combustion process, in accordance with the invention.

FIG. 2 represents the circuitry forming an alternative embodiment of the circuit in FIG. 1.

DETAILED DESCRIPTION OF A PREFERRED EMBODIMENT

Figure 3:
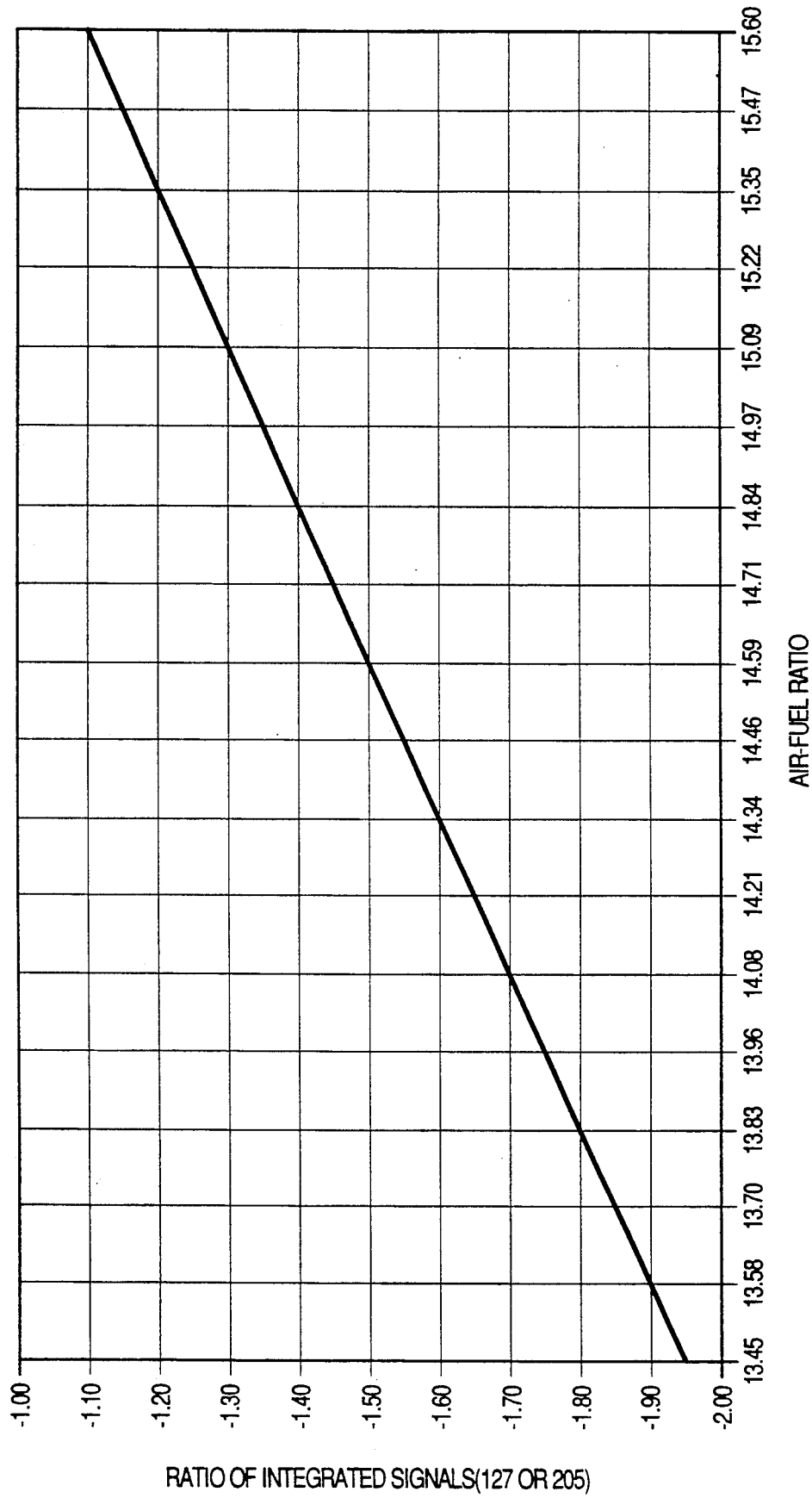
FIG. 3 is a graph illustrating the air-fuel ratio as detected with the apparatus of FIG. 1 or FIG. 2.

FIG. 1 is a schematic block diagram, illustrating a preferred embodiment of an improved apparatus 100 for directly measuring an air-fuel ratio of a combustion process, in an internal combustion engine. Essentially, the light output of the combustion process is measured continuously from two narrowband portions of the electromagnetic spectrum centered around two wavelengths. The ratio of the integrals of the signals emitted at these two wavelengths directly represents the air-fuel ratio of the combustion process. In the preferred embodiment, the wavelengths measured are within two regions of electromagnetic spectrum located at wavelengths between 580 nanometers to 800 nanometers and 900 nanometers to 1000 nanometers. Specifically, the wavelengths located near 930 nanometers and 720 nanometers are used here. Preferably, the narrowband regions are defined by a bandwidth of 10 nanometers, to extract the light intensity at the wavelengths of interest, however they may be as wide as 50 nanometers. Preferably, the first wavelength is spaced apart less than 420 nanometers from the second wavelength. The narrow separation between the two wavelengths ensures that the changes of transmissivity of the sensors, due to contamination from the combustion process, affects both wavelengths equally. Note that the two selected wavelengths are located in the vicinity of the infrared spectrum. Those of ordinary skill in the art may observe other pairs of wavelengths located within these two bands, that can be used to yield the same information.

In the preferred embodiment, a first electromagnetic wave sensing means 105, and second electromagnetic wave sensing means 115, are configured such that they receive the same information during the combustion process, from a substantially common physical location in a combustion chamber 101. In the preferred embodiment, these sensing means 105 and 115 are constructed of silicon photodetectors having filters attached thereto, the combination forming the detectors 105 and 115. That the detectors are positioned to monitor substantially the same location in order to receive the same information is important for the following reasons. When using more than one detector, the accuracy of the measurement can be affected by the location, thus the viewing field, that these detectors are directed towards. This is because the mixture for combustion is not homogeneously distributed throughout the combustion chamber. Further, during the combustion process, the measurable effect exhibits a dynamic gradient because of the traveling wave effect of the combustion process. Additionally, there may be contamination, which may be in the form of soot, present in the combustion chamber as a byproduct of combustion. This contamination may be different at different locations. Any gradients, or contamination will cause an error in the output of the detectors. For all of these reasons, it is important that the two detectors share a common viewing field, such that they receive the same information.

There are varied techniques to ensure that the detectors receive the same information during the combustion process. One means, is to position a light transmissive cable through the combustion chamber wall and then split the cable into the two remotely mounted detectors. Alternatively, the photodetectors may be contained in a housing in close proximity to the combustion chamber. In this case the light transmission is provided through a short rod of light transmissive material, typically sapphire. In the preferred embodiment the former technique is used. It is important to remember that whatever physical configuration is chosen, that the information received and further processed by the detectors must be substantially the same, in order to maximize accuracy.

The light information, provided during the combustion process, is transmitted via a fiber optic bundle 102, having good transmissivity at the required wavelengths. In this case, Anhydroguide G fiber from Fiberguide Industries is used. The fiber optic bundle 102 is terminated using standard SMA connectors for connection to the detectors 105 and 115. The end of the bundle terminated at the combustion chamber, is constructed with a modified SMA connector, that is provided with an extended ferrule. The ferrule is inserted into a housing 103, conveniently made to fit an access hole provided into the combustion chamber. The housing 103 terminates in a window, typically made of sapphire, which seals the housing 103 against combustion heat and pressure, but which passes the required wavelengths of light.

The fiber optic bundle 102 is bifurcated at 104, in order to transmit the same broadband electromagnetic radiation to the two detectors 105 and 115. Isolation of the required wavelengths is performed by passing the radiation output from each of the bifurcations through a narrowband interference filter, each filter centered on one of the wavelengths of interest and placed in front of a photodetector, forming the detectors 105 and 115. Such narrowband interference filters are supplied, for example, by Acton Research Corporation. Each detector, 105 and 115, will then be exposed to light at one of the two anticipated wavelengths.

The photodetector located in the detector 105, is constructed of a type S1722 device, supplied by Hamamatsu Corporation. A combination of a 930 nanometer narrowband interference filter and the S1722 photodetector enable the measurement of wavelengths in the vicinity of 930 nanometers. Of course, those of ordinary skill in the art will recognize other substantially equivalent means for achieving the same result. The detector 105 provides a first signal 107 representative of the light intensity emitted substantially proximate the wavelength of 930 nanometers. This first signal 107 is then amplified by an amplifier 109, then integrated by integrator 111. The integrator 111 integrates the signal 107 over the period of combustion, or a portion thereof, and outputs an amplified and integrated signal 113 that represents the light energy emitted proximate to 930 nanometers during the period of the combustion process, or a portion thereof. This is an analog integration because of the analog nature of the signal. This integration provides a more robust signal than that provided by measurement at a single point during the combustion process because integration provides an averaging effect over the entire combustion process. This means that transients, due to systemic noise or other influences will substantially not affect the accuracy of the measurement. The complimentary detector is described next.

The photodetector included in the detector 115, is also constructed of a S1722 type device. A combination of a 720 nanometer narrowband interference filter and the S1722 photodetector enable the measurement of wavelengths in the vicinity of 720 nanometers. The detector 115 provides a second signal 117 representative of the light intensity emitted substantially proximate the wavelength of 720 nanometers. This second signal 117 is then amplified by an amplifier 119, then integrated by integrator 121. The integrator 121 integrates the signal 117 over the period of combustion, or a portion thereof, and outputs an amplified and integrated signal 123 that represents the light energy emitted proximate to 720 nanometers during the period of the combustion process, or a portion thereof. This is also an analog integration because of the analog nature of the signal. Preferably the signal 117 is integrated substantially coincident with the integration of the signal 107.

The amplified integral of the first signal 113 representative of light energy emitted at substantially 930 nanometers, and the amplified integral of the second signal 123, representative of light energy emitted at substantially 720 nanometers, are further processed by a ratio circuit 125. The ratio circuit 125 divides the first signal 113 by the second signal 123. The resulting signal 127 is presented at the output of the ratio circuit 125. This signal 127 directly represents a measurement of the air-fuel ratio as measured during the combustion process. Measurement may either be taken on individual combustion cycles, or may be taken on successive combustion cycles and averaged.

The magnitude of this derived signal 127 is linearly proportional to the air-fuel ratio in the combustion chamber during the combustion process. The resultant air-fuel ratio may then be passed to an engine control system to be used as an indication of the air-fuel ratio, for the purposes of controlling of the air-fuel ratio to a desired target value. Because this signal 127 is linear, no additional resource burden, or accuracy degradation, is placed on conversion as it would require if the signal 127 was nonlinear. FIG. 3 shows the linear relationship between the ratioed integrals of the light intensity emitted at substantially 930 nanometers and 720 nanometers and air-fuel ratio.

An alternative embodiment 200 is suggested in FIG. 2. In this embodiment, the integration and ratioing of the two signals, representative of light intensity emitted at substantially 930 nanometers and substantially 720 nanometers during the combustion process, are conditional using a computer mechanism 203. An analog to digital converter 201 is used to convert the amplified analog signals 107 and 117 into the computer's 203 digital domain. The converter 201 successively converts the alternate signals presented from the amplifiers 109 and 119 and supplies them alternately to the computer 203. The computer 203 is programmed to execute the method steps necessary to reach an equivalent effect of the remaining apparatus of FIG. 1. These steps include integration and ratioing. The integration process is numerical because of the digital nature of the signal. Also, the numerical integration of the second signal is provided substantially coincident with the integration of the first signal. The result is output 205 in digital form and represents the air-fuel ratio measured during the combustion process. This signal may then be passed to an engine control system for further processing as mentioned earlier.

It can be seen that the apparatus in FIG. 1, or of FIG. 2 combined with the appropriate method steps, yield an elegant yet powerful mechanism to directly measure, on a linear scale, the air-fuel ratio during a combustion process. Integration provides a more robust signal than that provided by measurement at a single point during the combustion process, by reducing the effect on accuracy due to systemic noise or other transients. Further, by selecting a common field of view and selecting two proximate wavelengths the effect of contamination, resulting from combustion, is minimized. And finally, the linear nature of the resulting air-fuel ratio signal 127 ensures no loss of accuracy, or taxing of additional resources, that can be expected by post conversion.

What is claimed is:

1. An apparatus for directly measuring air-fuel ratio in an internal combustion engine combustion process comprising:

first electromagnetic wave sensing means providing a first signal representative of light intensity emitted at a first wavelength;

second electromagnetic wave sensing means providing a second signal representative of light intensity emitted at a second wavelength; and ratioing means for ratioing an integral of the first signal and an integral of the second signal and providing an air-fuel ratio signal, indicative of an air-fuel ratio during the combustion process.

2. An apparatus in accordance with claim 1 wherein the first wavelength is in the vicinity of the infrared spectrum.

3. An apparatus in accordance with claim 2 wherein the second wavelength is in the vicinity of the infrared spectrum.

4. An apparatus in accordance with claim 3 wherein the first wavelength is about 720 nanometers.

5. An apparatus in accordance with claim 3 wherein the first wavelength is between the range of 580 nanometers to 800 nanometers and the second wavelength is between 900 nanometers to 1,000 nanometers.

6. An apparatus in accordance with claim 2 wherein the first wavelength is about 930 nanometers.

7. An apparatus in accordance with claim 1 wherein the first wavelength is spaced apart less than 420 nanometers from the second wavelength.

8. An apparatus in accordance with claim 1 wherein said first electromagnetic wave sensing means and said second electromagnetic wave sensing means derive their signals from a substantially common physical location.

9. An apparatus in accordance with claim 1 wherein the integral of the first signal is performed by an analog integrator.

10. An apparatus in accordance with claim 9 wherein the integral of the second signal is provided by an analog integrator.

11. An apparatus in accordance with claim 10 wherein the integration of the second signal is provided substantially coincident with the integration of the first signal.

12. An apparatus in accordance with claim 1 wherein the integral of the first signal is performed by a numerical integrator.

13. An apparatus in accordance with claim 12 wherein the integral of the second signal is provided by an numerical integrator.

14. An apparatus in accordance with claim 13 wherein the integration of the second signal is provided substantially coincident with the integration of the first signal.

15. An apparatus in accordance with claim 1 wherein said first electromagnetic wave sensing means comprises a filter and a photodetector for determining the light intensity emitted at a first wavelength.

16. An apparatus in accordance with claim 15 wherein said filter has a bandwidth of 10 nanometers.

17. An apparatus in accordance with claim 15 wherein said filter has a bandwidth of less than 50 nanometers.

18. An apparatus in accordance with claim 1 wherein said second electromagnetic wave sensing means comprises a filter and a photodetector for determining the light intensity emitted at a second wavelength.

19. A method of determining air-fuel ratio from measurement of the combustion process in an internal combustion engine including the steps of:

measuring a first electromagnetic wavelength emitted from said combustion process and providing a first signal representative of light intensity emitted at said first electromagnetic wavelength;

measuring a second electromagnetic wavelength emitted from said combustion process and providing a second signal representative of light intensity emitted at said second electromagnetic wavelength; and ratioing, an integral of the first signal and an integral of the second signal and providing an air-fuel ratio signal, indicative of an air-fuel ratio in the combustion process.

* * * * *